United States Patent [19]

Hosoi

[11] Patent Number: 5,483,081

[45] Date of Patent: Jan. 9, 1996

[54] METHOD FOR DETECTING LIGHT EMITTED BY TWO SURFACES OF A STIMULABLE PHOSPHOR SHEET

[75] Inventor: Yuichi Hosoi, Kanagawa, Japan

[73] Assignee: Fuji Photo Film Co., Ltd., Kanagawa, Japan

[21] Appl. No.: 137,759

[22] Filed: Oct. 19, 1993

[30] Foreign Application Priority Data

Oct. 19, 1992 [JP] Japan ..................... 4-280285
Oct. 19, 1992 [JP] Japan ..................... 4-280286

[51] Int. Cl.$^6$ .................................. G01N 23/04
[52] U.S. Cl. .................. 250/585; 250/484.4; 250/487.1; 250/586
[58] Field of Search .................... 250/584, 585, 250/586, 484.4, 487.1, 488.1

[56] References Cited

U.S. PATENT DOCUMENTS

| | | | |
|---|---|---|---|
| 4,258,264 | 3/1981 | Kotera et al. | 250/484.4 |
| 4,276,473 | 6/1981 | Kato et al. | 250/327.1 |
| 4,315,318 | 2/1982 | Kato et al. | 364/515 |
| 4,346,295 | 8/1982 | Tanaka et al. | 250/327.2 |
| 4,387,428 | 6/1983 | Ishida et al. | 364/414 |
| 4,394,581 | 7/1983 | Takahashi et al. | 250/484.4 |

FOREIGN PATENT DOCUMENTS

| | | | |
|---|---|---|---|
| 56-11395 | 2/1981 | Japan . | |
| 2112800 | 4/1990 | Japan . | |
| 481833 | 3/1992 | Japan | 250/585 |
| 9006538 | 6/1990 | WIPO | 250/585 |

*Primary Examiner*—Carolyn E. Fields
*Attorney, Agent, or Firm*—Sughrue, Mion, Zinn, Macpeak & Seas

[57] ABSTRACT

A stimulable phosphor sheet comprises a stimulable phosphor layer, and a colored layer, which is located on one side of the stimulable phosphor layer and contains a coloring agent. The coloring agent is capable of selectively absorbing stimulating rays. The stimulable phosphor sheet is scanned with the stimulating rays from the side opposite to the colored layer. The light, which is emitted by the two surfaces of the stimulable phosphor sheet during its scanning with the stimulating rays, is photoelectrically detected from the two surfaces of the stimulable phosphor sheet, and an image signal representing the radiation image is thereby obtained. The sharpness of an image reproduced from the image signal is thereby efficiently kept high. A second embodiment provides an optical layer on a stimulable phosphor sheet, wherein the optical layer transmits only light which is incident from a direction substantially normal to the surface of the stimulable phosphor sheet. The optical layer prevents the rays which are irradiated from a side of the phosphor sheet having the optical layer from being reabsorbed by the phosphor sheet after reflecting from a photodetector which is located on the same side of the phosphor sheet as the optical layer and which detects light emitted from the phosphor sheet in response to stimulating rays.

10 Claims, 2 Drawing Sheets

METHOD FOR DETECTING LIGHT EMITTED BY TWO SURFACES OF A STIMULABLE PHOSPHOR SHEET

BACKGROUND OF THE INVENTION

1. Field of the Invention

This invention relates to a method for detecting light emitted by two surfaces of a stimulable phosphor sheet, on which a radiation image has been stored.

2. Description of the Prior Art

When certain kinds of phosphors are exposed to radiation such as X-rays, α-rays, β-rays, γ-rays, cathode rays or ultraviolet rays, they store part of the energy of the radiation. Then, when the phosphor which has been exposed to the radiation is exposed to stimulating rays, such as visible light, light is emitted by the phosphor in proportion to the amount of energy stored thereon during its exposure to the radiation. A phosphor exhibiting such properties is referred to as a stimulable phosphor.

As disclosed in U.S. Pat. Nos. 4,258,264, 4,276,473, 4,315,318, 4,387,428, and Japanese Unexamined Patent Publication No. 56(1981)-11395, it has been proposed to use stimulable phosphors in radiation image recording and reproducing systems. Specifically, a radiation image of an object, such as the human body, is stored on a sheet provided with a layer of the stimulable phosphor (hereinafter referred to as a stimulable phosphor sheet). The stimulable phosphor sheet is then scanned with stimulating rays, such as a laser beam, which cause it to emit light in proportion to the amount of energy stored thereon during its exposure to the radiation. The light emitted by the stimulable phosphor sheet when it is exposed to the stimulating rays is photoelectrically detected and converted into an electric image signal. The image signal is then processed and used during the reproduction of the radiation image of the object as a visible image, which has good image quality and can serve as an effective tool in, particularly, the efficient and accurate diagnosis of an illness. The ultimately obtained visible image may be reproduced as a hard copy or may be reproduced on a display device, such as a cathode ray tube (CRT) display device.

As a method for detecting light emitted by a stimulable phosphor sheet, a method has heretofore been known wherein a photoelectric read-out means for photoelectrically detecting the light emitted by the stimulable phosphor sheet is located only on the side of the stimulable phosphor sheet that is being scanned with the stimulating rays. The light emitted by one surface of the stimulable phosphor sheet is photoelectrically detected by the photoelectric read-out means. Also, a method for detecting light emitted by two surfaces of a stimulable phosphor sheet has been proposed in, for example, U.S. Pat. No. 4,346,295. With the proposed method for detecting light emitted by two surfaces of a stimulable phosphor sheet, two photoelectric read-out means are located on opposite sides of the stimulable phosphor sheet in order to photoelectrically detect the light emitted by the two surfaces of the stimulable phosphor sheet.

The method for detecting light emitted by two surfaces of a stimulable phosphor sheet has the advantages in that the efficiency, with which the light emitted by the stimulable phosphor sheet is guided and detected, can be kept high as a whole, and a high signal-to-noise (S/N) ratio can be obtained.

U.S. Pat. No. 4,394,581 discloses a technique wherein a radiation image storage panel (or a stimulable phosphor sheet) is colored with a coloring agent capable of selectively absorbing the stimulating rays such that an image having high sharpness can be obtained. In this publication, various embodiments are described wherein the layers constituting the radiation image storage panel, such as a phosphor layer, a protective layer, and a substrate, are colored. However, this publication does not describe anything about how the radiation image storage panel should be colored when the operation for detecting light emitted by two surfaces of the radiation image storage panel is to be carried out, nor does it suggest anything about how the radiation image storage panel should be colored when the operation for detecting light emitted by two surfaces of the radiation image storage panel is to be carried out.

Japanese Unexamined Patent Publication No. 2(1990)-112800 discloses a radiation image storage panel wherein a protective layer of the radiation image storage panel (or a stimulable phosphor sheet) is constituted of a material having fine light guiding path structures, which extend in a direction substantially normal to the surface of a phosphor layer, such that an image having good image quality can be obtained. However, this publication does not describe anything about the operation for photoelectrically detecting light emitted by two surfaces of the radiation image storage panel, nor does it suggest anything about the operation for detecting light emitted by two surfaces of the radiation image storage panel.

During the operation for detecting light emitted by two surfaces of a stimulable phosphor sheet, the problems occur in that the stimulating rays, which are scanning the stimulable phosphor sheet, pass through the stimulable phosphor sheet, impinge upon the photoelectric read-out means located facing the back surface of the stimulable phosphor sheet, and are reflected by the photoelectric read-out means. Specifically, the stimulating rays, which have been reflected and diffused by the photoelectric read-out means, impinge upon the portions of the stimulable phosphor sheet other than the portion that is being scanned, and cause these portions of the stimulable phosphor sheet to emit light. Therefore, image information, which is not to be detected at a given instant, is photoelectrically detected at the given instant from the two surfaces of the stimulable phosphor sheet. As a result, the sharpness of the ultimately obtained image cannot be kept high.

SUMMARY OF THE INVENTION

The primary object of the present invention is to provide a method for detecting light emitted by two surfaces of a stimulable phosphor sheet, wherein the sharpness of an ultimately obtained image is efficiently kept high.

Another object of the present invention is to provide a method for detecting light emitted by two surfaces of a stimulable phosphor sheet, wherein the signal-to-noise ratio is kept higher than when an operation for detecting light emitted by two surfaces of a stimulable phosphor sheet is carried out with a conventional stimulable phosphor sheet.

The present invention provides a first method for detecting light emitted by two surfaces of a stimulable phosphor sheet, comprising the steps of:

i) obtaining a stimulable phosphor sheet, which has been exposed to radiation carrying radiation image information and on which a radiation image has thereby been stored, the stimulable phosphor sheet comprising:

a) a stimulable phosphor layer, and b) a colored layer, which is located on one side of the stimulable phosphor layer and contains a coloring agent, the coloring agent being capable of selectively absorbing stimulating rays, which cause the stimulable phosphor layer to emit light in proportion to the amount of energy stored thereon during its exposure to the radiation, ii) scanning the stimulable phosphor sheet with the stimulating rays from the side opposite to the colored layer, and iii) photoelectrically detecting the light, which is emitted by the two surfaces of the stimulable phosphor sheet during the scanning of the stimulable phosphor sheet with the stimulating rays, from the two surfaces of the stimulable phosphor sheet, an image signal representing the radiation image being thereby obtained.

In the first method for detecting light emitted by two surfaces of a stimulable phosphor sheet in accordance with the present invention, of the stimulating rays, which cause the stimulable phosphor layer to emit light in proportion to the amount of energy stored thereon during its exposure to the radiation, and the light emitted by the stimulable phosphor layer, the stimulating rays are selectively absorbed by the coloring agent. The coloring agent must be capable of absorbing the stimulating rays. Even if the coloring agent also absorbs the light emitted by the stimulable phosphor layer, the absorptivity of the coloring agent with respect to the light emitted by the stimulable phosphor layer must be lower than the absorptivity with respect to the stimulating rays.

The colored layer of the stimulable phosphor sheet may be located such that it may be in contact with the stimulable phosphor layer. Alternatively, a different layer may intervene between the colored layer and the stimulable phosphor layer. Also, for example, the colored layer may be located as a substrate or a protective layer such that it may be in contact with the stimulable phosphor layer. Alternatively, the colored layer may be located as an adhesive layer, which adheres a substrate or a protective layer to the stimulable phosphor layer. As another alternative, the colored layer may be located on the side outward from the substrate or the protective layer. Specifically, as the stimulable phosphor sheet used in the first method for detecting light emitted by two surfaces of a stimulable phosphor sheet in accordance with the present invention, any stimulable phosphor sheet may be employed which comprises a stimulable phosphor layer and a colored layer located on one side of the stimulable phosphor layer.

With the first method for detecting light emitted by two surfaces of a stimulable phosphor sheet in accordance with the present invention, the stimulable phosphor sheet is used which comprises the stimulable phosphor layer and the colored layer containing the coloring agent capable of selectively absorbing the stimulating rays. The stimulable phosphor sheet, on which the radiation image has been stored, is scanned with the stimulating rays from the side opposite to the colored layer. The light, which is emitted by the two surfaces of the stimulable phosphor sheet during the scanning of the stimulable phosphor sheet with the stimulating rays, is photoelectrically detected from the two surfaces of the stimulable phosphor sheet. The stimulating rays, which pass through the stimulable phosphor sheet, are absorbed by the colored layer, and therefore little stimulating rays impinge upon the photoelectric read-out means, which is located at the back surface of the stimulable phosphor sheet. Even if part of the stimulating rays is reflected by the photoelectric read-out means and again impinges upon the stimulable phosphor sheet, such stimulating rays will be absorbed by the colored layer, and therefore little stimulating rays will again impinge upon the stimulable phosphor layer. Therefore, portions of the stimulable phosphor of the stimulable phosphor layer other than the portion that is being scanned can be prevented from being stimulated by the stimulating rays. Accordingly, with the first method for detecting light emitted by two surfaces of a stimulable phosphor sheet in accordance with the present invention, the sharpness of an ultimately obtained image can be efficiently kept high.

The present invention also provides a second method for detecting light emitted by two surfaces of a stimulable phosphor sheet, comprising the steps of:

i) obtaining a stimulable phosphor sheet, which has been exposed to radiation carrying radiation image information and on which a radiation image has thereby been stored, the stimulable phosphor sheet comprising:

a) a stimulable phosphor layer, and b) an optical layer, which is located on one side of the stimulable phosphor layer, the optical layer being capable of transmitting only light impinging thereupon from a direction which is normal thereto, ii) scanning the stimulable phosphor sheet with stimulating rays from the side opposite to the optical layer, the stimulating rays causing the stimulable phosphor layer to emit light in proportion to the amount of energy stored thereon during its exposure to the radiation, and iii) photoelectrically detecting the light, which is emitted by the two surfaces of the stimulable phosphor sheet during the scanning of the stimulable phosphor sheet with the stimulating rays, from the two surfaces of the stimulable phosphor sheet, an image signal representing the radiation image being thereby obtained.

The term "optical layer capable of transmitting only light impinging thereupon from a direction which is normal thereto" as used herein for the second method for detecting light emitted by two surfaces of a stimulable phosphor sheet in accordance with the present invention means a layer constituted of a material capable of confining light, which has entered from an input surface at an angle not larger than a specific angle (i.e. not larger than the maximum receptive angle) with respect to the line normal to the input surface, in regions inside of fine light guiding paths, and transmitting the confined light to an output surface. By way of example, the optical layer may be constituted of a crystal of ulexite, or the like, or an optical element, such as a fiber optics plate (F. O. P.). These materials have the properties such that they can confine light, which has entered from an input surface at an angle not larger than a specific angle (i.e. not larger than the maximum receptive angle) with respect to the line normal to the input surface, in regions inside of fine light guiding paths and can transmit the confined light to an output surface.

Ulexite is a hydrous sodium potassium borate mineral. The crystal of ulexite is of the triclinic system and has the optical properties described above.

The fiber optics plate (F. O. P.) is an optical element constituted of a plurality of fine fibers, each of which comprises a core glass having a high refractive index and a cladding glass having a low refractive index and covering the core glass, and which are fused together. (The core diameter falls within the range of 6 μm to 25 μm.)

Either one of the two materials described above can be employed in the second method for detecting light emitted by two surfaces of a stimulable phosphor sheet in accordance with the present invention. However, ulexite has the drawbacks in that it is not easily available and in that the durability of the crystal is not high due to its brittleness and its slight solubility in water. Therefore, in the second method for detecting light emitted by two surfaces of a stimulable phosphor sheet in accordance with the present invention, the fiber optics plate should preferably be employed.

The material described above can also confine light, which has entered from the output surface due to reflection, or the like, in the light guiding paths and can transmit the confined light to the input surface. The material is described in detail in Japanese Unexamined Patent Publication No. 2(1990)-112800.

The optical layer of the stimulable phosphor sheet employed in the second method for detecting light emitted by two surfaces of a stimulable phosphor sheet in accordance with the present invention is constituted of a material such as those described above.

With the second method for detecting light emitted by two surfaces of a stimulable phosphor sheet in accordance with the present invention, during the operation for reading out the radiation image stored on the stimulable phosphor sheet, the stimulable phosphor sheet is scanned with the stimulating rays from the side opposite to the optical layer during the operation for reading out the radiation image stored on the stimulable phosphor sheet. Therefore, only the stimulating rays, which have passed through the stimulable phosphor layer and impinge at an angle not larger than the maximum receptive angle upon the optical layer, are confined in the fine light guiding paths and are radiated out of the stimulable phosphor sheet without being diffused. A photoelectric read-out means for detecting the light emitted by the stimulable phosphor sheet is located at the back surface of the stimulable phosphor sheet so as to stand facing a source of the stimulating rays with the stimulable phosphor sheet intervening therebetween. The stimulating rays, which have been radiated out of the stimulable phosphor sheet, impinge upon the photoelectric read-out means and are reflected by the photoelectric read-out means towards the optical layer of the stimulable phosphor sheet. However, the stimulating rays, which have been reflected and diffused by the photoelectric read-out means and which impinge at an angle larger than the maximum receptive angle of the optical layer, do not impinge upon the stimulable phosphor layer from the back surface of the stimulable phosphor sheet. Accordingly, the sharpness of the ultimately obtained image can be prevented from becoming low due to the stimulating rays, which are reflected by the photoelectric read-out means located at the back surface of the stimulable phosphor sheet and impinge upon the back surface of the stimulable phosphor sheet.

DESCRIPTION OF THE PREFERRED EMBODIMENTS

The present invention will hereinbelow be described in further detail with reference to the accompanying drawings.

Figure 1:
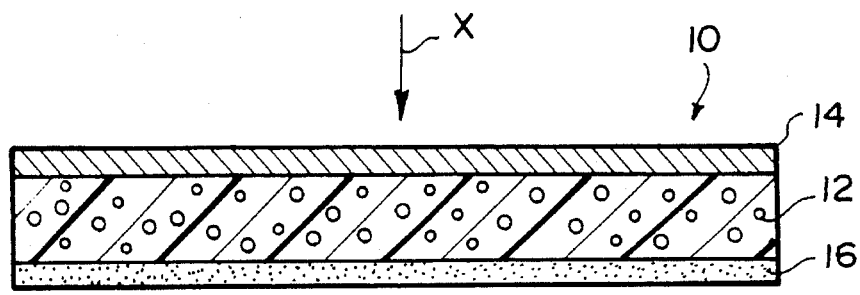
FIG. 1 is a sectional view showing an example of a stimulable phosphor sheet employed in an embodiment of the first method for detecting light emitted by two surfaces of a stimulable phosphor sheet in accordance with the present invention.

FIG. 1 is a sectional view showing an example of a stimulable phosphor sheet employed in an embodiment of the first method for detecting light emitted by two surfaces of a stimulable phosphor sheet in accordance with the present invention.

With reference to FIG. 1, a stimulable phosphor sheet 10 comprises a stimulable phosphor layer 12 and a protective layer 14, which is overlaid on one surface of the stimulable phosphor layer 12. The stimulable phosphor sheet 10 also comprises a colored layer 16, which is overlaid on the other surface of the stimulable phosphor layer 12 and which contains a coloring agent capable of selectively absorbing stimulating rays. In FIG. 1, the arrow X represents the direction, from which the stimulating rays are irradiated to the stimulable phosphor sheet 10 and scan it. The colored layer 16 may also serve as a substrate or a protective layer for the stimulable phosphor layer 12. The coloring agent contained in the colored layer 16 can selectively absorb the stimulating rays.

Figure 2:
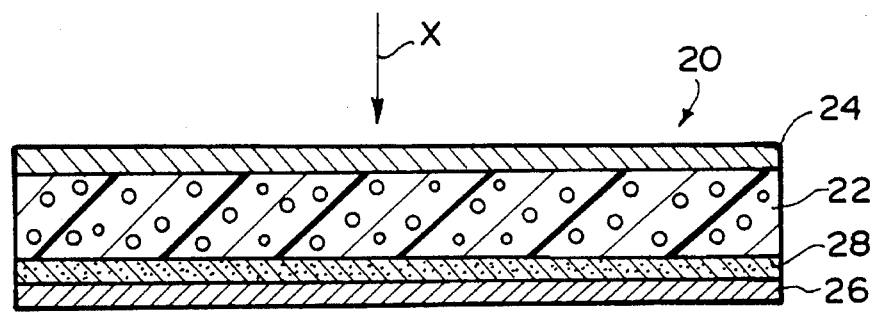
FIG. 2 is a sectional view showing a different example of a stimulable phosphor sheet employed in an embodiment of the first method for detecting light emitted by two surfaces of a stimulable phosphor sheet in accordance with the present invention.

FIG. 2 is a sectional view showing a different example of a stimulable phosphor sheet employed in an embodiment of the first method for detecting light emitted by two surfaces of a stimulable phosphor sheet in accordance with the present invention.

With reference to FIG. 2, a stimulable phosphor sheet 20 comprises a stimulable phosphor layer 22, and a protective layer 24, which is overlaid on one surface of the stimulable phosphor layer 22. The stimulable phosphor sheet 20 also comprises a colored layer 28, which is overlaid on the other surface of the stimulable phosphor layer 22 and which contains a coloring agent capable of selectively absorbing stimulating rays. The stimulable phosphor sheet 20 further comprises a protective layer (or a substrate) 26, which is overlaid on the colored layer 28. In FIG. 2, the arrow X represents the direction, from which the stimulating rays are irradiated to the stimulable phosphor sheet 20 and scan it. The colored layer 28 may also serve as an adhesive layer for adhering the protective layer (or the substrate) 26 to the stimulable phosphor layer 22. Alternatively, the colored layer 28 may be merely located as an intermediate layer. As a further different example of the stimulable phosphor sheet, the protective layer (or the substrate) 26 may be overlaid directly on the other surface of the stimulable phosphor layer 22, and the colored layer 28 may be overlaid on the protective layer (or the substrate) 26 on the side opposite to the stimulable phosphor layer 22.

How an X-ray image of an object is stored on the stimulable phosphor sheet will be described hereinbelow.

Ordinarily, the stimulable phosphor sheet is housed in a cassette, which blocks the stimulating rays, such as visible light. In this state, the stimulable phosphor sheet is used during an operation for recording an X-ray image. An X-ray source and the cassette, in which the stimulable phosphor sheet has been housed, are located facing each other such that an object lying on an image recording table may intervene between the X-ray source and the cassette. At this time, the colored layer of the stimulable phosphor sheet housed in the cassette may be located on the front side or on the back side of the stimulable phosphor layer. X-rays are then produced by the X-ray source and irradiated to the object. The X-rays, which have passed through the object, impinge upon the stimulable phosphor sheet housed in the cassette. In this manner, an X-ray image of the object is stored on the stimulable phosphor sheet.

Figure 3:
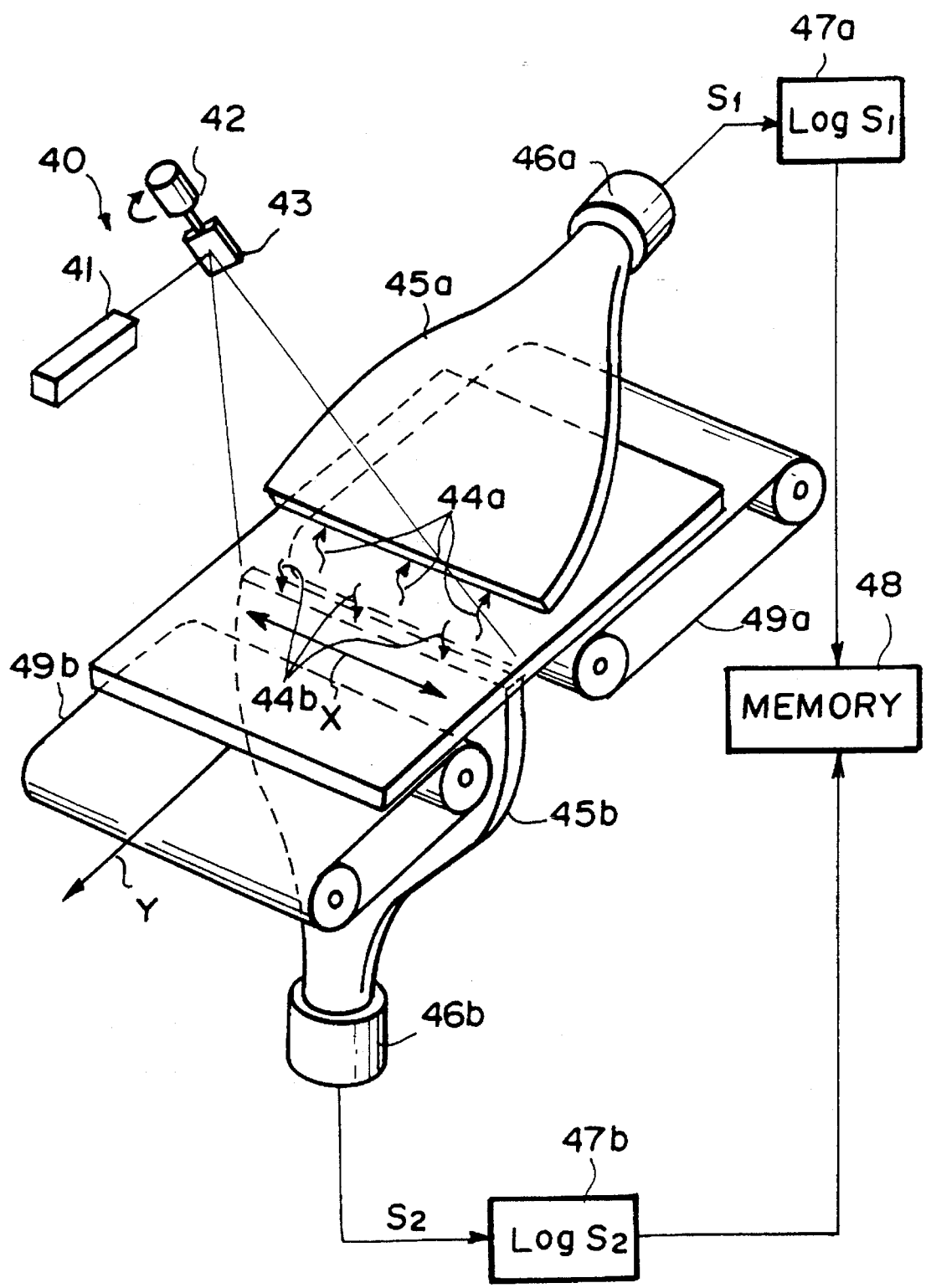
FIG. 3 is a schematic view showing an example of an X-ray image read-out apparatus.

FIG. 3 is a schematic view showing an example of an X-ray image read-out apparatus for photoelectrically reading out the X-ray image from the stimulable phosphor sheet 10, on which the X-ray image has been stored in the manner described above.

With reference to FIG. 3, the stimulable phosphor sheet 10 is placed on endless belts 49a and 49b such that the colored layer may face down. The endless belts 49a and 49b are rotated by motors (not shown). A laser beam source 41, a rotating polygon mirror 43, and a motor 42 are located above the stimulable phosphor sheet 10. The laser beam source 41 produces a laser beam serving as stimulating rays, which cause the stimulable phosphor sheet 10 to emit light in proportion to the amount of energy stored thereon during its exposure to the X-rays. The rotating polygon mirror 43 reflects and deflects the laser beam, which has been produced by the laser beam source 41, such that the laser beam may scan the stimulable phosphor sheet 10 in main scanning directions. The motor 42 rotates the rotating polygon mirror 43. A light guide member 45a is located above and close to the position on the stimulable phosphor sheet 10 which is being scanned with the laser beam. The light guide member 45a collects light, which is emitted by the stimulable phosphor sheet 10 when it is scanned with the laser beam, from above the stimulable phosphor sheet 10. Also, a light guide member 45b is located below the position on the stimulable phosphor sheet 10 which is being scanned with the laser beam. The light guide member 45b is located perpendicularly to the stimulable phosphor sheet 10 and collects the light, which is emitted by the stimulable phosphor sheet 10 when it is scanned with the laser beam, from below the stimulable phosphor sheet 10. The light guide members 45a and 45b are located such that they may respectively be in close contact with photomultipliers 46a and 46b, which photoelectrically detect the light emitted by the stimulable phosphor sheet 10. The photomultipliers 46a and 46b are respectively connected to logarithmic amplifiers 47a and 47b. The logarithmic amplifiers 47a and 47b are connected to a memory 48.

How the X-ray image is read out from the stimulable phosphor sheet 10 in the X-ray image read-out apparatus will be described hereinbelow with reference to FIG. 3. The X-ray image recording operation is carried out in the manner described above, and the X-ray image of the object is stored on the stimulable phosphor sheet 10. The stimulable phosphor sheet 10, on which the X-ray image has been stored, is set at a predetermined position on the endless belts 49a and 49b. The stimulable phosphor sheet 10, which has been set at the predetermined position, is conveyed by the endless belts 49a and 49b in a sub-scanning direction indicated by the arrow Y. Also, the laser beam is produced by the laser beam source 41. The laser beam, which has been produced by the laser beam source 41, is reflected and deflected by the rotating polygon mirror 43, which is quickly rotated by the motor 42 in the direction indicated by the arrow. The laser beam, which has thus been reflected and deflected by the rotating polygon mirror 43, impinges upon the stimulable phosphor sheet 10 and scans it in the main scanning directions indicated by the double headed arrow X. The main scanning directions are approximately normal to the sub-scanning direction indicated by the arrow Y. When the stimulable phosphor sheet 10 is exposed to the laser beam, the exposed portion of the stimulable phosphor sheet 10 emits light in proportion to the amount of energy stored thereon during its exposure to the X-rays. The light, which is emitted upwardly by the stimulable phosphor sheet 10, is represented by reference numeral 44a. The light, which is emitted downwardly by the stimulable phosphor sheet 10, is represented by reference numeral 44b. The emitted light 44a is guided by the light guide member 45a and photoelectrically detected by the photomultiplier 46a. The light guide member 45a is made from a light guiding material, such as an acrylic plate. The light guide member 45a has a linear input end face, which is located such that it may extend along the main scanning line on the stimulable phosphor sheet 10, and a ring-like output end face, which is located such that it may be in close contact with a light receiving face of the photomultiplier 46a. The emitted light 44a, which has entered from the input end face into the light guide member 45a, is guided through repeated total reflection inside of the light guide member 45a, emanates from the output end face, and is received by the photomultiplier 46a. The amount of the emitted light 44a representing the X-ray image is converted by the photomultiplier 46a into an electric signal. In the same manner as that described above, the emitted light 44b is guided by the light guide member 45b and is photoelectrically detected by the photomultiplier 46b.

The stimulable phosphor sheet 10, which is employed in the embodiment of the first method for detecting light emitted by two surfaces of a stimulable phosphor sheet in accordance with the present invention, is provided with the colored layer 16 containing the coloring agent capable of selectively absorbing the stimulating rays. When the X-ray image is read out from the stimulable phosphor sheet 10, the stimulable phosphor sheet 10 is located with its colored layer 16 facing down such that the stimulable phosphor sheet 10 may be scanned with the stimulating rays from the side opposite to the colored layer 16 of the stimulable phosphor sheet 10. Therefore, the stimulating rays, which have been produced by the laser beam source 41 and have passed through the protective layer 14 and the stimulable phosphor layer 12, are absorbed by the colored layer 16 of the stimulable phosphor sheet 10. If the stimulating rays are radiated out of the back side of the stimulable phosphor sheet 10 and are reflected by the photoelectric read-out means, which is located on the back side of the stimulable phosphor sheet 10, the stimulating rays will again impinge upon the stimulable phosphor sheet 10. However, such stimulating rays are absorbed by the colored layer 16 and do not impinge upon the stimulable phosphor layer 12.

The photomultiplier 46a generates an analog output signal S1. The analog output signal S1 is logarithmically amplified by the logarithmic amplifier 47a and is then fed into the memory 48. In the memory 48, the analog output signal S1 is converted by an A/D converter into a digital signal, and a first image signal is thereby obtained. Also, the photomultiplier 46b generates an analog output signal S2. The analog output signal S2 is logarithmically amplified by the logarithmic amplifier 47b and is then fed into the memory 48. In the memory 48, the analog output signal S2 is converted by an A/D converter into a digital signal, and a second image signal is thereby obtained. The first and second image signals are added to each other by a calculating means of the memory 48, and an ultimate image signal is thereby obtained. The level of the ultimate image signal is proportional to the logarithmic value of the amount of the light emitted by each picture element on the stimulable phosphor sheet 10. In this manner, the light emitted by the stimulable phosphor sheet 10 during its exposure to the stimulating rays is detected from the two surfaces of the stimulable phosphor sheet 10. Therefore, the efficiency, with which the light emitted by the stimulable phosphor sheet 10 is guided and detected, can be kept high, and an image having a high S/N ratio can be obtained ultimately. In particular, as described above, the light guide member 45b guides the light, which is emitted by the stimulable phosphor sheet 10 without being adversely affected by the stimulating rays reflected and diffused by the light guide member 45b. Therefore, an image can be obtained which has a higher sharpness than that obtainable with a conventional method for detecting light emitted by two surfaces of a stimulable phosphor sheet.

Stimulable phosphor sheets provided with stimulable phosphor layers colored with coloring agents have heretofore been used widely. In cases where light emitted by two surfaces of such a conventional stimulable phosphor sheet is detected, the colored stimulable phosphor layer absorbs the stimulating rays, which pass through the stimulable phosphor sheet, and adverse effects from the stimulating rays reflected by a photoelectric read-out means, which is located on the back side of the stimulable phosphor sheet, can be reduced. Therefore, an image can be obtained which has as high a sharpness as that obtained with the first method for detecting light emitted by two surfaces of a stimulable phosphor sheet in accordance with the present invention. However, in such cases, the coloring agent contained in the stimulable phosphor layer directly reduces the amount of the stimulating rays, which scan the stimulable phosphor sheet and impinge upon the stimulable phosphor layer. Accordingly, the amount of light emitted by the stimulable phosphor sheet becomes smaller, and the S/N ratio of the image signal obtained in this manner becomes lower than the S/N ratio obtained with the first method for detecting light emitted by two surfaces of a stimulable phosphor sheet in accordance with the present invention.

An embodiment of the second method for detecting light emitted by two surfaces of a stimulable phosphor sheet in accordance with the present invention will be described hereinbelow.

Figure 4:
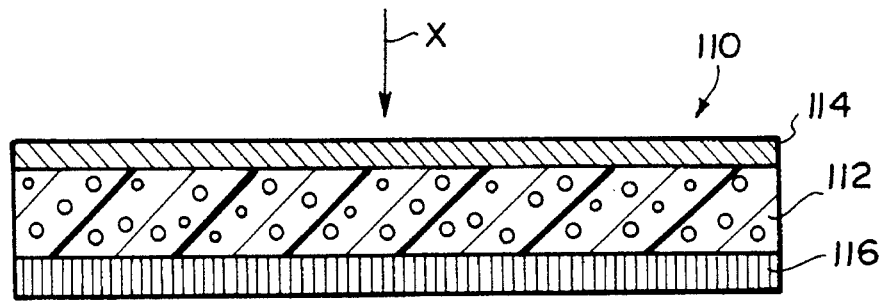
FIG. 4 is a sectional view showing an example of a stimulable phosphor sheet employed in an embodiment of the second method for detecting light emitted by two surfaces of a stimulable phosphor sheet in accordance with the present invention.

FIG. 4 is a sectional view showing an example of a stimulable phosphor sheet employed in an embodiment of the second method for detecting light emitted by two surfaces of a stimulable phosphor sheet in accordance with the present invention.

With reference to FIG. 4, a stimulable phosphor sheet 110 comprises a stimulable phosphor layer 112 and a protective layer 114, which is overlaid on one surface of the stimulable phosphor layer 112. The stimulable phosphor sheet 110 also comprises an optical layer 116, which is overlaid on the other surface of the stimulable phosphor layer 112. The optical layer 116 is constituted of a material having fine light guiding path structures, which extend in a direction substantially normal to the surface of the stimulable phosphor layer 112. A protective layer or a substrate may be located on the side outward from the optical layer 116. In this embodiment, the optical layer 116 is located such that it may be in direct contact with the stimulable phosphor layer 112. Alternatively, a substrate, a protective layer, or an adhesive layer, which adheres the optical layer 116 and the stimulable phosphor layer 112 to each other, may be located between the optical layer 116 and the stimulable phosphor layer 112. In the second method for detecting light emitted by two surfaces of a stimulable phosphor sheet in accordance with the present invention, any stimulable phosphor sheet may be employed which comprises the stimulable phosphor layer and the aforesaid optical layer located on one side of the stimulable phosphor layer.

Figure 5:
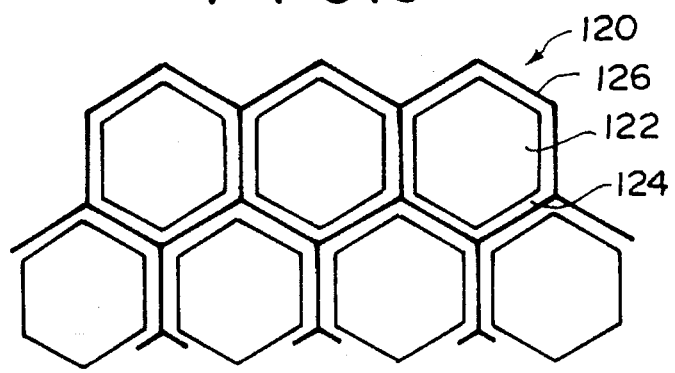
FIG. 5 is an explanatory view showing a fiber optics plate, the view being taken from the direction of an input (or output) surface of the fiber optics plate.

FIG. 5 is an explanatory view showing a fiber optics plate which constitutes the optical layer 116, the view being taken from the direction of an input (or output) surface of the fiber optics plate.

With reference to FIG. 5, a fiber comprises a core glass 122, which has a high refractive index, and a cladding glass 124, which has a low refractive index and which surrounds the core glass 122. A plurality of such fibers are located adjacent to one another with an absorber (E. M. A.) glass 126 intervening between adjacent fibers. The absorber glass 126 absorbs light, which goes from the core glass 122 through the cladding glass 124 to the exterior, or light impinging upon the cladding glass 124. Specifically, light, which has entered into a single fiber from its input surface, does not go to different fibers, and is confined in the region inside of the fine light guiding path (i.e. the fiber). The confined light is transmitted to the output surface of the fiber and is radiated to the side outward from the output surface of the fiber.

In this manner, light impinging upon the fiber optics plate is divided by the respective fibers, transmitted to the output surface, and radiated out of the output surface. Therefore, light is not diffused.

How an X-ray image of an object is stored on the stimulable phosphor sheet will be described hereinbelow.

Ordinarily, the stimulable phosphor sheet is housed in a cassette, which blocks the stimulating rays, such as visible light. In this state, the stimulable phosphor sheet is used during an operation for recording an X-ray image. An X-ray source and the cassette, in which the stimulable phosphor sheet has been housed, are located facing each other such that an object lying on an image recording table may intervene between the X-ray source and the cassette. At this time, the optical layer of the stimulable phosphor sheet housed in the cassette may be located on the front side or on the back side of the stimulable phosphor layer. X-rays are then produced by the X-ray source and irradiated to the object. The X-rays, which have passed through the object, impinge upon the stimulable phosphor sheet housed in the cassette. In this manner, an X-ray image of the object is stored on the stimulable phosphor sheet.

An operation for reading out the X-ray image from the stimulable phosphor sheet 110, on which the X-ray image has been stored in the manner described above, is carried out in the same manner as that described above with reference to FIG. 3 for the stimulable phosphor sheet 10. At this time, the stimulable phosphor sheet 110 is placed on the endless belts 49a and 49b such that the optical layer (i.e. the fiber optics plate) may face down.

The stimulable phosphor sheet 110, which is employed in the embodiment of the second method for detecting light emitted by two surfaces of a stimulable phosphor sheet in accordance with the present invention, is provided with the optical layer 116 capable of transmitting only light, which is incident from a direction substantially normal to the surface of the stimulable phosphor layer 112. When the X-ray image stored on the stimulable phosphor sheet 110 is to be read out, the stimulable phosphor sheet 110 is located with its optical layer 116 facing down, and the stimulating rays are irradiated to the stimulable phosphor sheet 110 from the side of the protective layer 114. At this time, the stimulating rays, which have been produced by the laser beam source 41 and have passed through the protective layer 114, the stimulable phosphor layer 112, and the optical layer 116, will be reflected by the light guide member 45b, which is located adjacent to the optical layer 116, and will again impinge upon the optical layer 116. However, at this time, the stimulating rays impinge upon the optical layer 116 at an angle larger than the maximum receptive angle of the optical layer 116 and, therefore, do not impinge upon the stimulable phosphor layer 12.

In this manner, the light emitted by the stimulable phosphor sheet 110 during its exposure to the stimulating rays is detected from the two surfaces of the stimulable phosphor sheet 110. Therefore, the efficiency, with which the light emitted by the stimulable phosphor sheet 110 is guided and detected, can be kept high, and an image having a high S/N ratio can be obtained ultimately. In particular, as described above, the light guide member 45b guides the light, which is emitted by the stimulable phosphor sheet 110 without being adversely affected by the stimulating rays reflected and diffused by the light guide member 45b. Therefore, an image can be obtained which has a higher sharpness than that obtainable with a conventional method for detecting light emitted by two surfaces of a stimulable phosphor sheet.

What is claimed is:

1. A method for detecting light emitted by two surfaces of a stimulable phosphor sheet, comprising the steps of:
   i) obtaining a stimulable phosphor sheet, which has been exposed to radiation carrying radiation image information and on which a radiation image has thereby been stored, the stimulable phosphor sheet comprising:
      a) a stimulable phosphor layer, and
      b) a colored layer, which is located on one side of the stimulable phosphor layer and contains a coloring agent, the coloring agent being capable of selectively absorbing stimulating rays, which cause the stimulable phosphor layer to emit light in proportion to the amount of energy stored thereon during its exposure to the radiation,
   ii) scanning the stimulable phosphor sheet with the stimulating rays from the side opposite to the colored layer, and
   iii) photoelectrically detecting the light, which is emitted by the two surfaces of the stimulable phosphor sheet during the scanning of the stimulable phosphor sheet with the stimulating rays, from the two surfaces of the stimulable phosphor sheet, an image signal representing the radiation image being thereby obtained.

2. A method as defined in claim 1 wherein the radiation image is an X-ray image.

3. A method as defined in claim 1 wherein the stimulating rays is a laser beam.

4. A method as defined in claim 1 wherein the stimulable phosphor sheet is two-dimensionally scanned with the stimulating rays.

5. A method for detecting light emitted by two surfaces of a stimulable phosphor sheet, comprising the steps of:
   i) obtaining a stimulable phosphor sheet, which has been exposed to radiation carrying radiation image information and on which a radiation image has thereby been stored, the stimulable phosphor sheet comprising:
      a) a stimulable phosphor layer, and
      b) an optical layer, which is located on one side of the stimulable phosphor layer, the optical layer being capable of transmitting only light impinging thereupon from a direction which is normal thereto,
   ii) scanning the stimulable phosphor sheet with stimulating rays from the side opposite to the optical layer, the stimulating rays causing the stimulable phosphor layer to emit light in proportion to the amount of energy stored thereon during its exposure to the radiation, and
   iii) photoelectrically detecting a first light, which is emitted by the surface of the stimulable phosphor sheet on which the optical layer is located using a first photodetection apparatus, and photoelectrically detecting a second light which is emitted by a second surface of the stimulable phosphor sheet opposite the first surface using a second photodetection apparatus, said detecting of the first and second lights occurring during the scanning of the stimulable phosphor sheet with the stimulating rays, wherein said optical layer prevents the stimulating rays from reflecting from the first photodetector apparatus and re-entering said stimulable phosphor layer, and obtaining an image signal representing the radiation image from the detected first and second lights.

6. A method as defined in claim 5 wherein the optical layer is constituted of a material capable of confining light, which has entered from an input surface of the optical layer at an angle not larger than a specific angle with respect to the line normal to the input surface, in regions inside of fine light guiding paths, and transmitting the confined light to an output surface of the optical layer.

7. A method as defined in claim 6 wherein the optical layer is constituted of a material selected from the group consisting of a crystal of ulexite and a fiber optics plate.

8. A method as defined in claim 5 wherein the radiation image is an X-ray image.

9. A method as defined in claim 5 wherein the stimulating rays is a laser beam.

10. A method as defined in claim 5 wherein the stimulable phosphor sheet is two-dimensionally scanned with the stimulating rays.

* * * * *